(12) United States Patent
Bahar et al.

(10) Patent No.: US 12,123,617 B2
(45) Date of Patent: *Oct. 22, 2024

(54) COOLING SYSTEMS HAVING AN INTEGRATED IONIC LIQUID SALT DEHUMIDIFICATION SYSTEM

(71) Applicant: FFI IONIX IP, INC., Wilmington, DE (US)

(72) Inventors: Bamdad Bahar, Georgetown, DE (US); William Parmelee, Orleans, MA (US); Omar Abdelaziz, Oak Ridge, TN (US); Qu Ming, Oak Ridge, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/231,069

(22) Filed: Aug. 7, 2023

(65) Prior Publication Data
US 2023/0383963 A1    Nov. 30, 2023

Related U.S. Application Data

(63) Continuation of application No. 17/503,678, filed on Oct. 18, 2021, now Pat. No. 11,719,447, which is a (Continued)

(51) Int. Cl.
*F24F 3/14* (2006.01)
*B01D 1/14* (2006.01)
(Continued)

(52) U.S. Cl.
CPC .............. *F24F 3/1417* (2013.01); *B01D 1/14* (2013.01); *B01D 5/0003* (2013.01); (Continued)

(58) Field of Classification Search
CPC .. F24F 3/1417; F24F 3/001; F24F 2003/1458; F24F 2003/1435; B01D 1/14; B01D 5/0003; B01D 5/0027; B01D 5/0039; B01D 5/0087; B01D 5/009; B01D 53/263; B01D 53/268; B01D 2252/30; C07D 233/58; C08L 27/12; F25B 17/02
See application file for complete search history.

(56) References Cited

U.S. PATENT DOCUMENTS

| | | | |
|---|---|---|---|
| 2011/0132027 A1* | 6/2011 | Gommed | F28D 21/0015 62/477 |
| 2015/0233589 A1* | 8/2015 | Betts | F24F 3/1417 202/180 |
| 2016/0054012 A1* | 2/2016 | LePoudre | F24F 3/147 62/271 |

* cited by examiner

*Primary Examiner* — Emmanuel E Duke

(57) ABSTRACT

A cooling system utilizes an organic ionic salt composition for dehumidification of an airflow. The organic ionic salt composition absorbs moisture from an inlet airflow to produce an outlet airflow with a reduce moisture from that of the inlet airflow. The organic ionic salt composition may be regenerated, wherein the absorbed moisture is expelled by heating with a heating device. The heating device may be an electrochemical heating device, such as a fuel cell, an electrochemical metal hydride heating device, an electrochemical heat pump or compressor, or a condenser of a refrigerant cycle, which may utilize an electrochemical pump or compressor. The efficiency of the cooling system may be increased by utilization of the waste heat the cooling system. The organic ionic salt composition may circulate back and forth or in a loop between a conditioner, where it absorbs moisture, to a regenerator, where moisture is desorbed by heating.

20 Claims, 18 Drawing Sheets

Related U.S. Application Data continuation of application No. 15/798,123, filed on Oct. 30, 2017, now Pat. No. 11,149,970.

(60) Provisional application No. 62/413,986, filed on Oct. 28, 2016.

(51) Int. Cl.
| | |
|---|---|
| *B01D 5/00* | (2006.01) |
| *B01D 53/26* | (2006.01) |
| *C07D 233/58* | (2006.01) |
| *C08L 27/12* | (2006.01) |
| *F25B 17/02* | (2006.01) |
| *F24F 3/00* | (2006.01) |

(52) U.S. Cl.
CPC ......... *B01D 5/0027* (2013.01); *B01D 5/0039* (2013.01); *B01D 5/0087* (2013.01); *B01D 5/009* (2013.01); *B01D 53/263* (2013.01); *B01D 53/268* (2013.01); *C07D 233/58* (2013.01); *C08L 27/12* (2013.01); *F25B 17/02* (2013.01); *B01D 2252/30* (2013.01); *F24F 3/001* (2013.01); *F24F 2003/1458* (2013.01)

COOLING SYSTEMS HAVING AN INTEGRATED IONIC LIQUID SALT DEHUMIDIFICATION SYSTEM

CROSS-REFERENCE TO RELATED APPLICATIONS

The application is a continuation of U.S. application Ser. No. 17/503,678 filed on Oct. 18, 2021, which is a continuation of U.S. Pat. No. 15,798,123 filed on Oct. 30, 2017 and now issued as U.S. Pat. No. 11,149,970 on Oct. 19, 2021, which claims the benefit of U.S. provisional patent application No. 62/413,986, and filed on Oct. 28, 2016, both entitled Cooling Systems Having An Integrated Ionic Liquid Salt Dehumidification System.

STATEMENT REGARDING FEDERALLY SPONSORED RESEARCH OR DEVELOPMENT

This invention was made with government support under Grant no. DE-EE0007040 awarded by Department of Energy. The government has certain rights in the invention.

FIELD OF THE INVENTION

The present invention relates to a cooling system that incorporates an integrated organic liquid salt dehumidification system

BACKGROUND

Desiccant systems are widely used to absorb moisture in environments and can be used to reduce the latent cooling load on HVAC systems; however, current technology use large amounts of heat to regenerate the desiccant. Conventional air conditioning systems use vapor compression refrigeration (VCR) cycles to remove moisture from humid air through condensation. This requires inefficient cooling and reheating of the air. One of the keys to creating higher efficiency cooling systems is to dehumidify air without over-cooling. Conventional HVAC systems achieve cooling and dehumidification by cooling the air below its dew point to condense the moisture and then reheat the air to provide it at the desired conditions. Historically, ordinary (hydroscopic) salts, such as NaCl, LiCl, LiBr etc., have been used in HVAC applications as an alternative means of dehumidifying the environment. This system has been termed an 'ILD' for ionic liquid dehumidification system operating in conjunction with a heat pump, wherein, the heat from the heat pump system is used to re-generate the ionic liquid. Separate sensible and latent cooling dehumidify air as close, adiabatic if possible, and then sensibly cool it at higher evaporating temperature.

SUMMARY OF THE INVENTION

The invention is directed to a cooling system that incorporates an integrated ionic liquid salt dehumidification system. An exemplary ionic liquid desiccant, or organic liquid salt, is a salt that comprises organic cations and inorganic or organic anions. These organic liquids salts are thermally stable, have low vapor pressure, are not corrosive to metals and have low driving temperatures to achieve dew point temperatures. A class of ionic salts have been identified that provide efficient moisture uptake and release that make them well suited for incorporation into a cooling system or a heating ventilation and cooling, HVAC system.

Ionic liquid desiccants, or organic liquid salts, are evaluated and described in publication hereinafter Qu: Ming Qu, et al, Aqueous Solution of [EMIM][OAc]: Property Formulations for use in air conditioning equipment design, Journal, Applied Thermal Engineering 124 (2017) pages 271-278, 2017; the entirety of which is hereby incorporated by reference herein. The organic liquid salts evaluated in this paper are identified in FIGS. 1 and 2. After extensive investigations of these thirteen different ionic liquid desiccants, 1-Ethyl-3-methylimidazolium acetate [EMIM][OAc], FIG. 2, was identified to exhibit the highest capacity to absorb and desorb water vapor under realistic operating regimes and can be regenerated by using low grade heat. As provided in this paper, 1-Ethyl-3-methylimidazolium acetate has a molecular mass of 170.21. In addition, some relevant properties and performance characteristics from this paper are provided Table 1 to 4.

TABLE 1

Summary of moisture adsorption of ionic liquids.

| Ionic liquids | EMIm TFSI | HMIm TFSI | MPPy TFSI | HMpy TFSI | BMIm Tf | EMIm BF4 | HMIm BF4 |
|---|---|---|---|---|---|---|---|
| Initial water content (ppm) | 43 | 46 | 54 | 46 | 116 | 318 | 252 |
| Maximum Adsorption (wt. %) | 99.24 | 99.48 | 99.52 | 99.77 | 94.89 | 91.15 | 93.69 |
| Minimum adsorption (wt. %) | 99.92 | 99.91 | 99.97 | 99.98 | 99.94 | 98.78 | 99.20 |
| Working Range (wt. %) | 0.68 | 0.43 | 0.45 | 0.21 | 5.05 | 7.63 | 5.51 |

Moisture adsorption = IL/(IL + $H_2O$) * 100.

TABLE 2

| Ionic liquids | EMIm $OA_C$ | HMIm $OA_C$ | EMIm ES | BMIm Ms | EMIm DEP | BMIm DBP |
|---|---|---|---|---|---|---|
| Initial water content (ppm) | 1265 | 249 | 266 | 435 | 515 | 443 |
| Maximum Adsorption (wt. %) | 67.66 | 84.86 | 78.64 | 76.21 | 75.28 | 86.25 |
| Minimum adsorption (wt. %) | 91.09 | 86.67 | 95.53 | 93.93 | 92.32 | 97.35 |
| Working Range (wt. %) | 23.43 | 11.81 | 16.89 | 17.72 | 17.04 | 11.1 |

TABLE 3

| 1-Ethyl-3-methylimidazolium acetate, $C_8H_{14}N_2O_2$ | | | | | |
|---|---|---|---|---|---|
| $\rho$ (g/cm³) | T (K) | $\eta_D$ (cp) | T (K) | K (S/m) | T (K) |
| 1.03 [12] | 298.15 | 162 [11]<br>91 [12] | 293.15<br>298.15 | 0.28 [11] | 293.15 |

TABLE 4

| $T_m$ (K) |
|---|
| 228.15 [24, 42] |
| 259.15 [7] |
| 253.15 [12] |

FIGS. 3 to 18 provide specific detail regarding a preferred ionic salt, EMIM Oac, 1-Ethyl-3-methylimidazolium acetate, as well as details of this salt in a binary mixture with water. The ionic salts or ionic salt mixtures may be used to absorb moisture from an inlet air flow that is cooled by a condenser or other cooling device and the ionic salt of salt mixtures may be regenerated by a heating device. A vapor compression cycle, or refrigerant cycle, comprises a condenser, wherein a vapor is condensed wherein a latent heat of vaporization may be used to regenerate the ionic salt composition. The condenser may be in thermal communication with the ionic salt composition, as described herein, to regenerate the salt so that it may absorb more moisture. The salt or a binary salt mixture composition may be circulated to absorb moisture from the air or vapor to be cooled and then passed by a heating device, such as a condenser, fuel cell, electrochemical pump, metal hydride heating device, for example to desorb the moisture from the ionic salt, or binary salt mixture.

An exemplary cooling system comprises a dehumidification system comprising an organic ionic salt composition that absorbs moisture from an inlet airflow. The cooling system comprises a cooling device such as an evaporator and a heating device that regenerators the organic ionic salt composition by heating it to drive out moisture. The organic ionic salt composition may be configured to flow back and forth or in a loop between a conditioner to a regenerator. In the conditioner, the organic ionic salt composition absorbs moisture and in the regenerator, moisture is expelled or reduced from the organic ionic salt composition. The conditioner may be coupled with an airflow through a cooling system. The outlet airflow from the cooling system is cooler and has a lower humidity or moisture content than the inlet airflow to the cooling system, as the moisture is removed by the ionic liquid dhimmification system.

The cooling system may be a traditional refrigeration system having a compressor, a condenser, an evaporator, and an expansion valve. The cooling device may be the evaporator and the heating device used in the regenerator may be the condenser. The refrigerant cycle may incorporate a traditional compressor or preferably an electrochemical compressor, as it is more efficient. The heat from the electrochemical compressor and/or the condenser may be used in a regenerator to expel moisture from the ionic liquid desiccant, such as organic liquid salt composition.

In another embodiment, the heating device of the regenerator is a fuel cell, such as polymer electrolyte membrane fuel cell. The waste heat from the fuel cell may be in thermal communication with the organic liquid salt composition to drive out moisture and the energy produced from the fuel cell may be used in the cooling system, such as to drive pumps, operate switches and the like.

In another embodiment, the heating device is a metal hydride heating device. A metal hydride may be contained in an enclosure and when hydrogen is absorbed it may generate heat that can be used to regenerate the organic liquid salt composition. In one embodiment, a metal hydride system comprise two enclosures for metal hydride and hydrogen is pumped back and forth or in a loop between them, wherein one enclosure generates heat and one absorbs heat. Therefore, the organic liquid salt composition may be exposed to the heating enclosure and the endothermic enclosure may be used to cool an airflow, or used as a cooling device as used herein. Valves may be used to control the flow of the organic liquid salt composition to the appropriate metal hydride enclosure. Likewise, valves may be used to control the flow of airflow over the appropriate metal hydride enclosure to cool the airflow.

An exemplary organic liquid salt composition comprises an organic ionic salt that is mixed with a liquid, such as water. Exemplary organic ionic salts are detailed, but not limited to those shown in FIGS. 1 and 2. Organic ionic salts may be mixed with water to produce a binary mixture that can be pumped from a conditioner to a regenerator.

An exemplary cooling system comprises a dehumidification loop, wherein the organic liquid salt composition flows from a conditioner, wherein it is exposed to the inlet air to absorb humidity from the inlet air, to a regenerator, wherein the organic liquid salt composition is in thermal communication with the heating device to desorb the absorbed moisture of the organic ionic salt.

The cooling system, as describe herein, may comprise or incorporate any of the components describe in the references incorporated by reference herein. This application incorporates by reference the entirety of U.S. application Ser. No. 15/289,220, filed on Oct. 10, 2016 and entitled Electrochemical Heat Transfer System, U.S. application Ser. No. 13/029,006 filed on Feb. 16, 2011 entitled Electrochemical Heat Transfer System, U.S. Pat. No. 8,627,671 issued on Jan. 14, 2014 and entitled Self-Contained Electrochemical Heat Transfer System, U.S. Application No. 61/215,131 filed on May 1, 2009, and U.S. application Ser. No. 13/029,006, U.S. Application No. 61/305,410, filed on Feb. 17, 2010 and entitled Electrochemical Heat Pump System for Cooling Electronic Components, and to U.S. Application No. 61/347,428, filed May 23, 2010 and entitled Compact Cooling Systems Using Electrochemical Compression.

This application incorporates by reference the entirety of U.S. provisional patent application No. 62/277,399, to Xergy Inc., filed on Jan. 11, 2016 and entitled Hydrogen Sorption and Desorption Heat Pump System, U.S. provisional patent application No. 62/288,417 to Xergy Inc., filed on Jan. 28, 2016 and entitled Electrochemical Compressor Driven Metal Hydride Heating Element For Heating and Cooling Applications, U.S. provisional patent application No. 62/292,529, to Xergy Inc., filed on Feb. 8, 2016, and entitled Advanced Metal Hydride Heat Pump Using Electrochemical Hydrogen Compressor, U.S. provisional patent application No. 62/297,123, to Xergy Inc., filed on Feb. 18, 2016 and entitled Hydrogen Sorption and Desorption Heat Pump System, U.S. provisional patent application No. 62/300,082, to Xergy Inc., filed on Feb. 26, 2016 and entitled Advanced Metal Hydride Heat Pump Using Electrochemical Hydrogen Compressor, U.S. provisional patent application No. 62/303,300, to Xergy Inc., filed on Mar. 3, 2016 and entitled Plate and Frame Metal Hydride Heat Exchanger, U.S. provisional patent application No. 62/308, 060, to Xergy Inc., filed on Mar. 14, 2016 and entitled Advanced Hydride Hot Water Heater, U.S. provisional patent application No. 62/315,664, to Xergy Inc., filed on Mar. 30, 2016 and entitled Water Management Apparatus For Metal Hydride Heat Exchangers With Electrochemical Compressor, U.S. provisional patent application No. 62/324,337, to Xergy Inc., filed on Apr. 18, 2016 and entitled High Efficiency Heat Pump, and U.S. provisional patent application No. 62/326,532, to Xergy Inc., filed on Apr. 22, 2016 and entitled Nickel Metal Hydride Heat pump.

This application incorporates by reference the entirety of U.S. provisional patent application No. 62/244,709, filed on Oct. 21, 2015 and entitled System and Method of Water Purification Utilizing an Ionomer Membrane, U.S. provisional patent application No. 62/385,178, filed on Sep. 8, 2016 and entitled Electrochemical Desalination System and U.S. provisional patent application No. 62/385,176, filed on Sep. 8, 2016 and entitled Ozone Generator System.

This application incorporates by reference the entirety of U.S. patent application Ser. No. 15/475,124, filed on Mar. 30, 2017, entitled Heat Pumps Utilizing Ionic Liquid Desiccant and currently pending.

An exemplary cooling system of the present inventions comprises an ionic liquid dehumidification system comprising an ionic liquid desiccant composition comprising an ionic liquid desiccant and water. The ionic liquid desiccant is pumped from a conditioner, where it absorbs moisture from a conditioner fluid, to a regenerator, where moisture is desorbed or driven out from the ionic liquid desiccant, such as into a regenerator fluid. An exemplary ionic liquid desiccant dehumidification system comprises exchangers, or exchange modules for the transfer to and from the ionic liquid desiccant. An exchange module comprises an impermeable exchange membrane having no bulk flow of air therethrough. An exemplary impermeable exchange membrane has a Gurley Densometer value of more than about 500 seconds and preferably more than 1000 seconds, thereby having no bulk flow of air through the thickness. This test can be performed on a Gurley Densometer, such as an automatic Gurley Densometer, model 4340 from Gurley Instruments, Inc. Water may absorb into the impermeable exchange membrane and pass therethrough, however air and gas will not flow through the membrane. An exemplary impermeable exchange membrane has little porosity, such as no more than about 10% porosity and preferably no more than about 5% or 2%. An exemplary impermeable exchange membrane comprises a continuous film of polymer that can seal air from one side to the opposing side. The exchange membrane may comprise a cation exchange or conductive polymer, such as ionomer, such as perfluorosulfonic acid polymer, ie. Nafion. The exchange membrane may comprise an anion exchange or anion conductive polymer, as detailed in applications incorporated by reference herein. The exchange membrane may a high moisture transport polymers such as urethane, or silicone, for example. An exemplary impermeable exchange membrane is very thin to promote high rates of moisture transport therethrough and is no more than 30 microns and preferably no more than 25 microns, or no more than 20 microns, such as 15 microns or less. To provide additional support for these thin impermeable exchange membranes, a support layer may be coupled with the exchange polymer, such as the ionomer. A support layer may be embedded partially or completely within the exchange polymer or ionomer. A support layer may be exposed on one or both sides of the exchange membrane. An exemplary support layer is a porous non-woven material, such as a fluoropolymer membrane, available from W. L. Gore and Associates, or Cellguard, available from 3M.

In an exemplary exchange module, conditioner fluid, such as air that is cooled and dehumidified flows past one side of an exemplary impermeable exchange membrane and ionic liquid desiccant flows past the opposing side. Water from the conditioner air passes through the impermeable exchange membrane and into the ionic liquid desiccant. The ionic liquid desiccant is then transferred to the regenerator module wherein a regenerator fluid flows past one side to absorb moisture from the ionic liquid desiccant. The ionic liquid desiccant may be heated in a regenerator, such as prior to entering the exchange module or exchanger or within the exchanger. A heating device may be thermally coupled with the regenerator to heat the ionic liquid desiccant. The heating device may be a resistive heater, or may be a device used in a refrigeration system or in the ionic liquid desiccant dehumidification system, such as waste heat from a pump, a controller, a compressor, and the like. A heating device may be a compressor of a refrigeration system and this compressor may be an electrochemical compressor. A heating device maybe a metal hydride heating element. A heating device may be a pump for pumping the ionic liquid desiccant or a working fluid or refrigerant through a refrigerant system.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
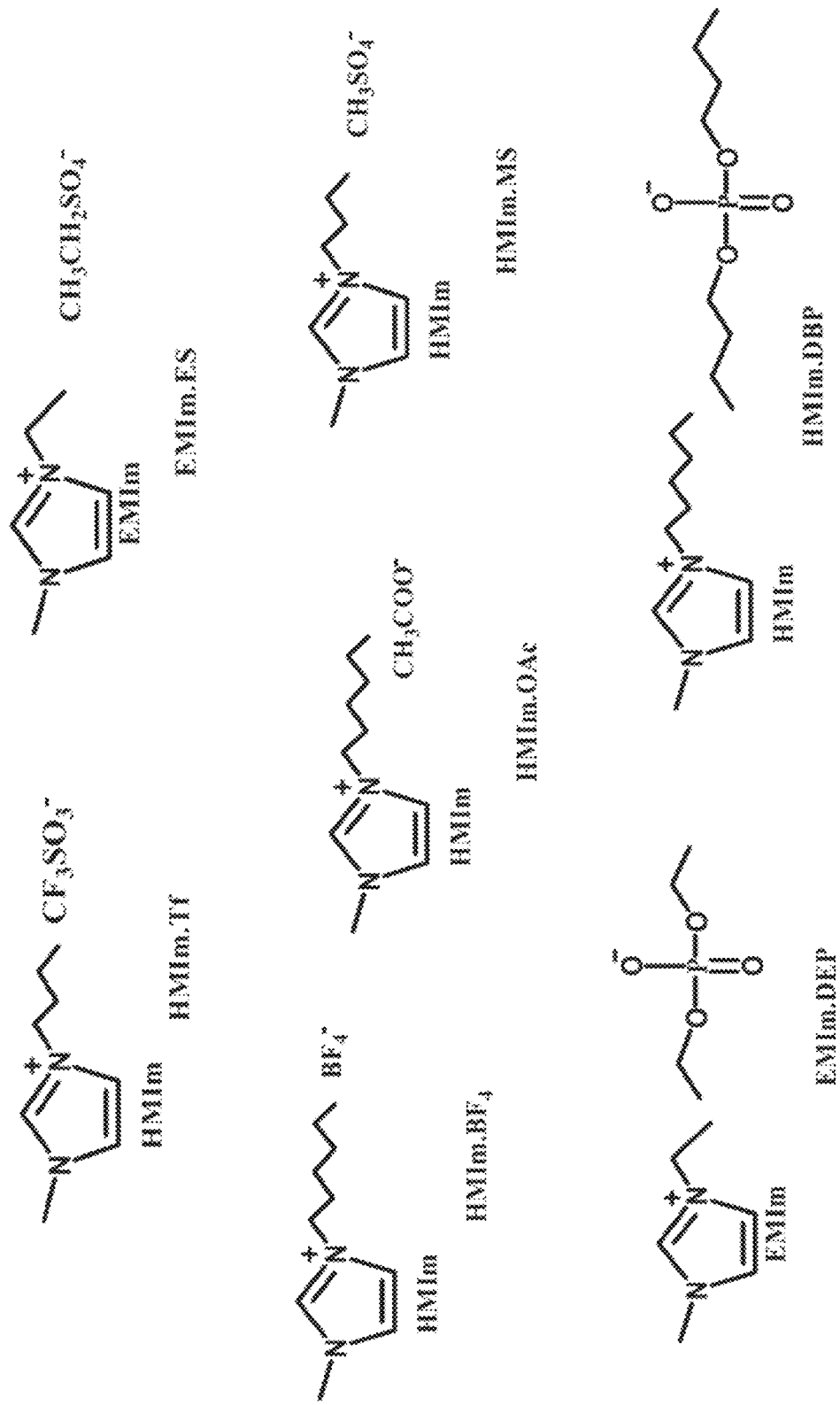
FIGS. 1 and 2 show the chemical diagram of some preferred organic ionic salt as described in the present invention.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

In cases where the present specification and a document incorporated by reference include conflicting and/or inconsistent disclosure, the present specification shall control.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

Figure 2:
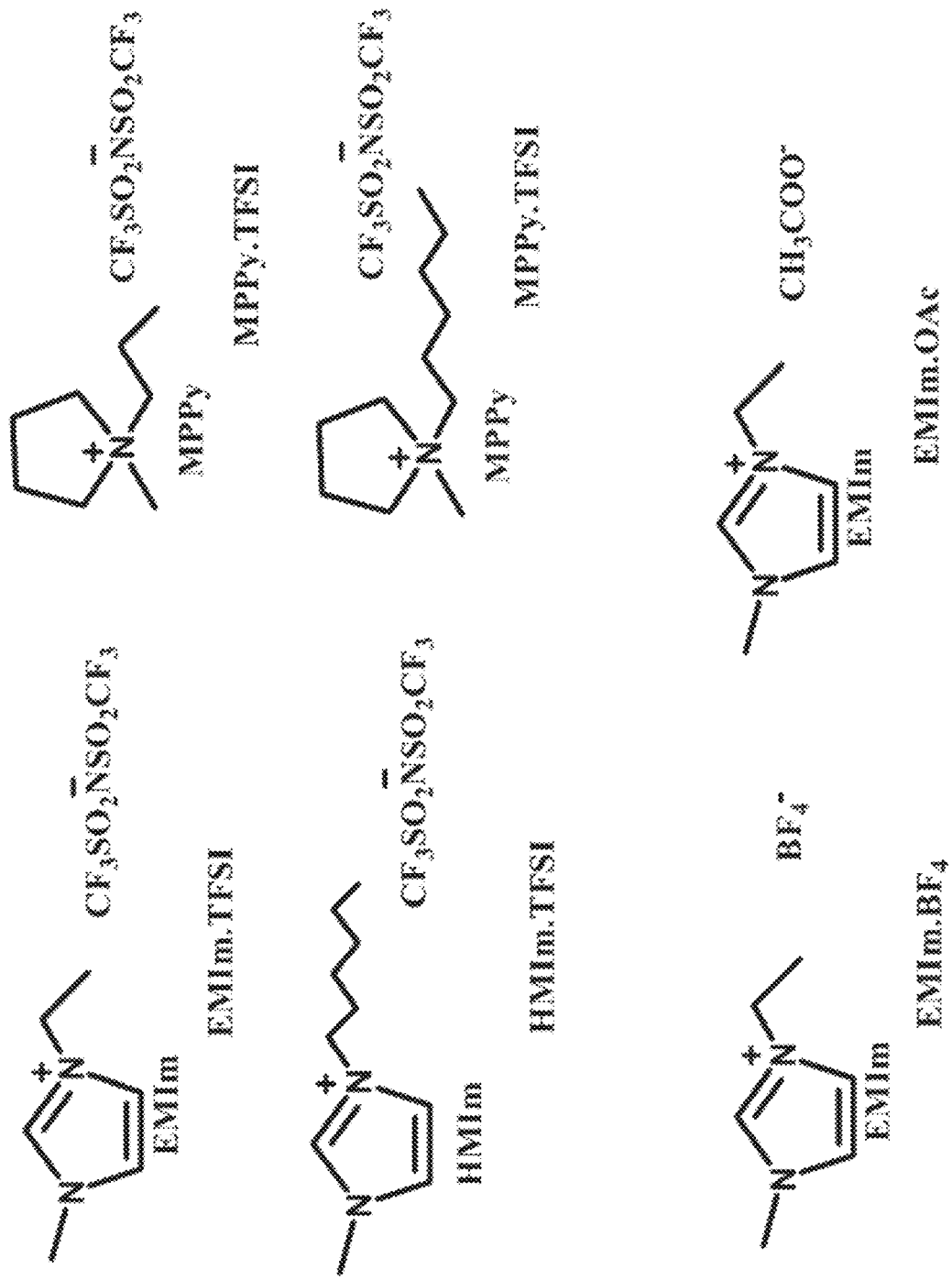

FIGS. 1 and 2 show the chemical diagram of some preferred organic ionic salt as described in the present invention.

Figure 3:
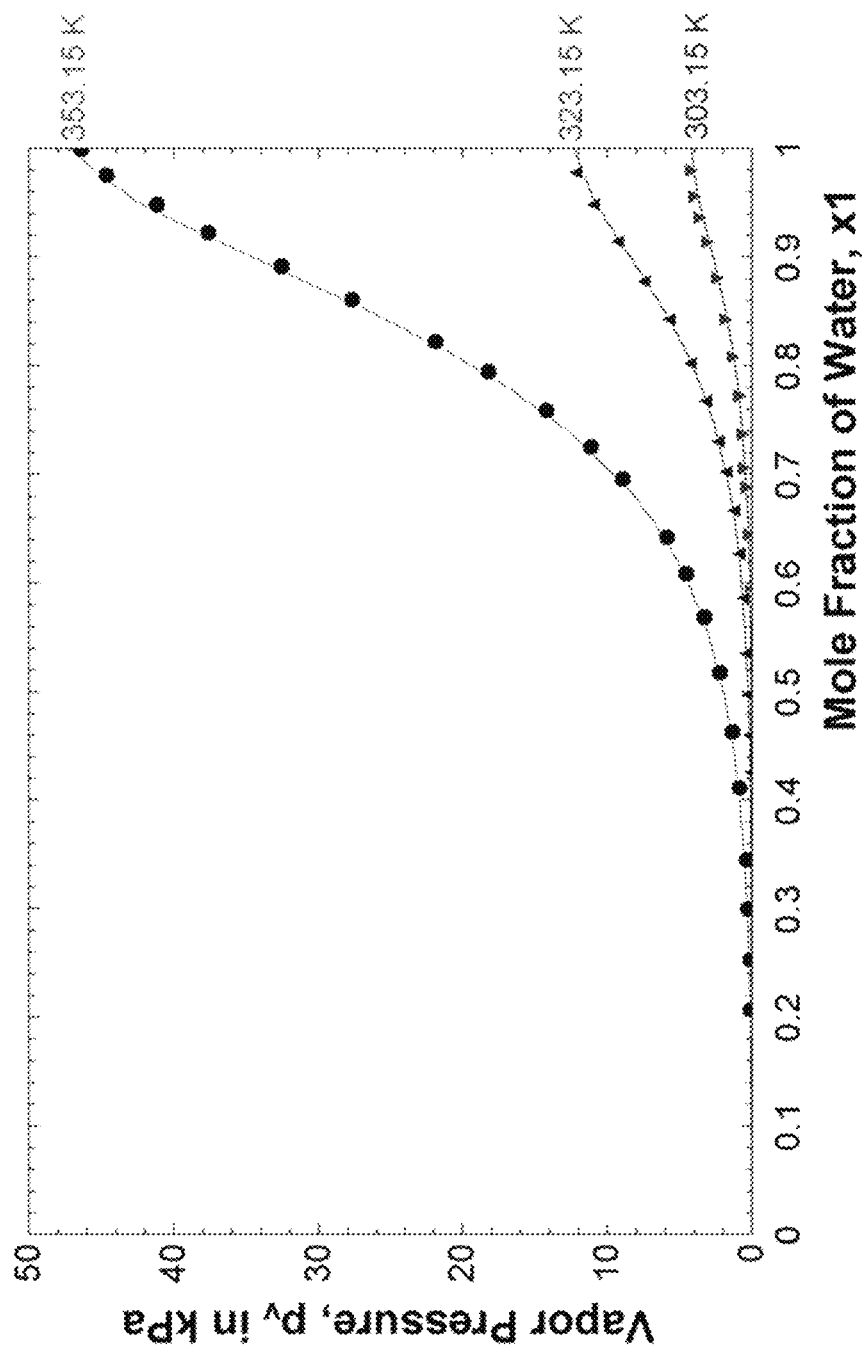
FIGS. 3 and 4 show graphs of vapor pressure verus mass fraction of water and EMIM Oac, 1-Ethyl-3-methylimidazolium acetate respectively.
Figure 4:
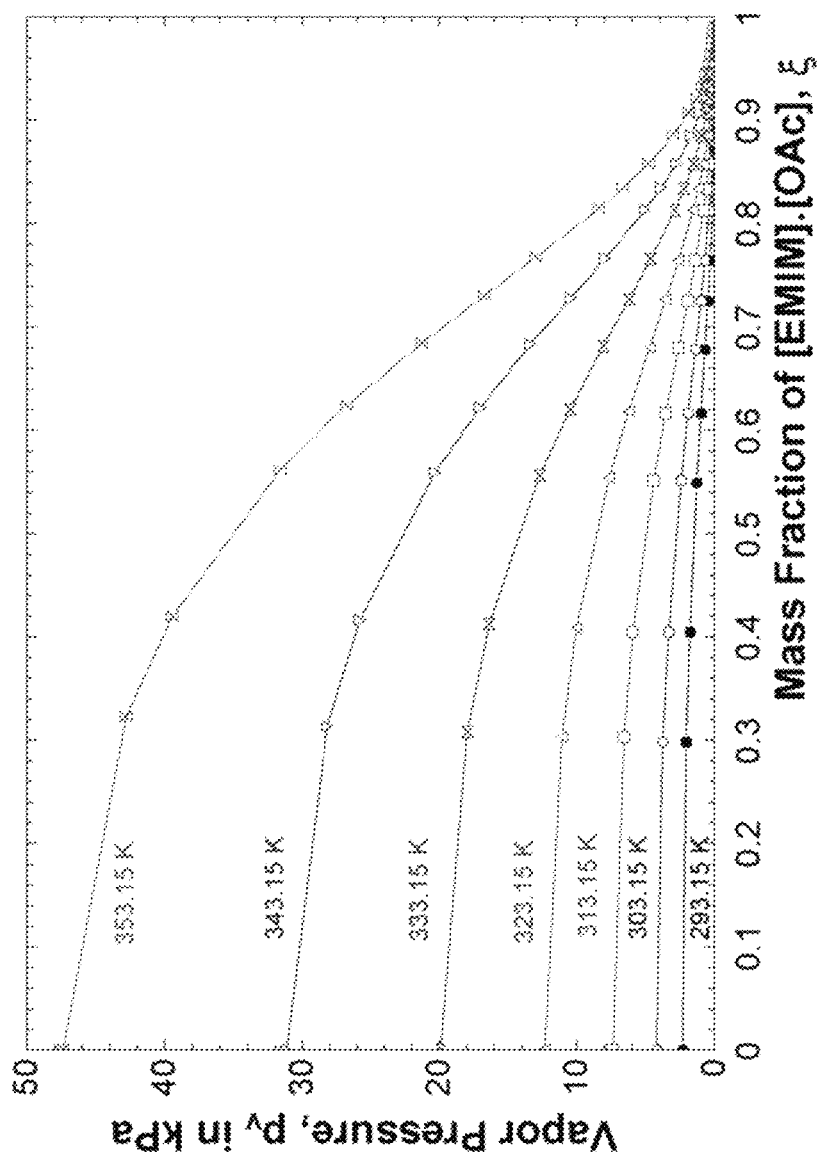

FIGS. 3 and 4 show graphs of vapor pressure verus mass fraction of water and EMIM Oac, 1-Ethyl-3-methylimidazolium acetate respectively. These figures are from the following paper: 1. Christiane Römich, et al., Thermodynamic Properties of Binary Mixtures of Water and Room-Temperature Ionic Liquids: Vapor Pressures, Heat Capacities, Densities, and Viscosities of Water+1-Ethyl-3-methylimidazolium Acetate and Water+Diethylmethylammonium Methane Sulfonate *J. Chem. Eng. Data,* 2012, 57 (8), pp 2258-2264, the entirety of which is hereby incorporated by reference.

Figure 5:
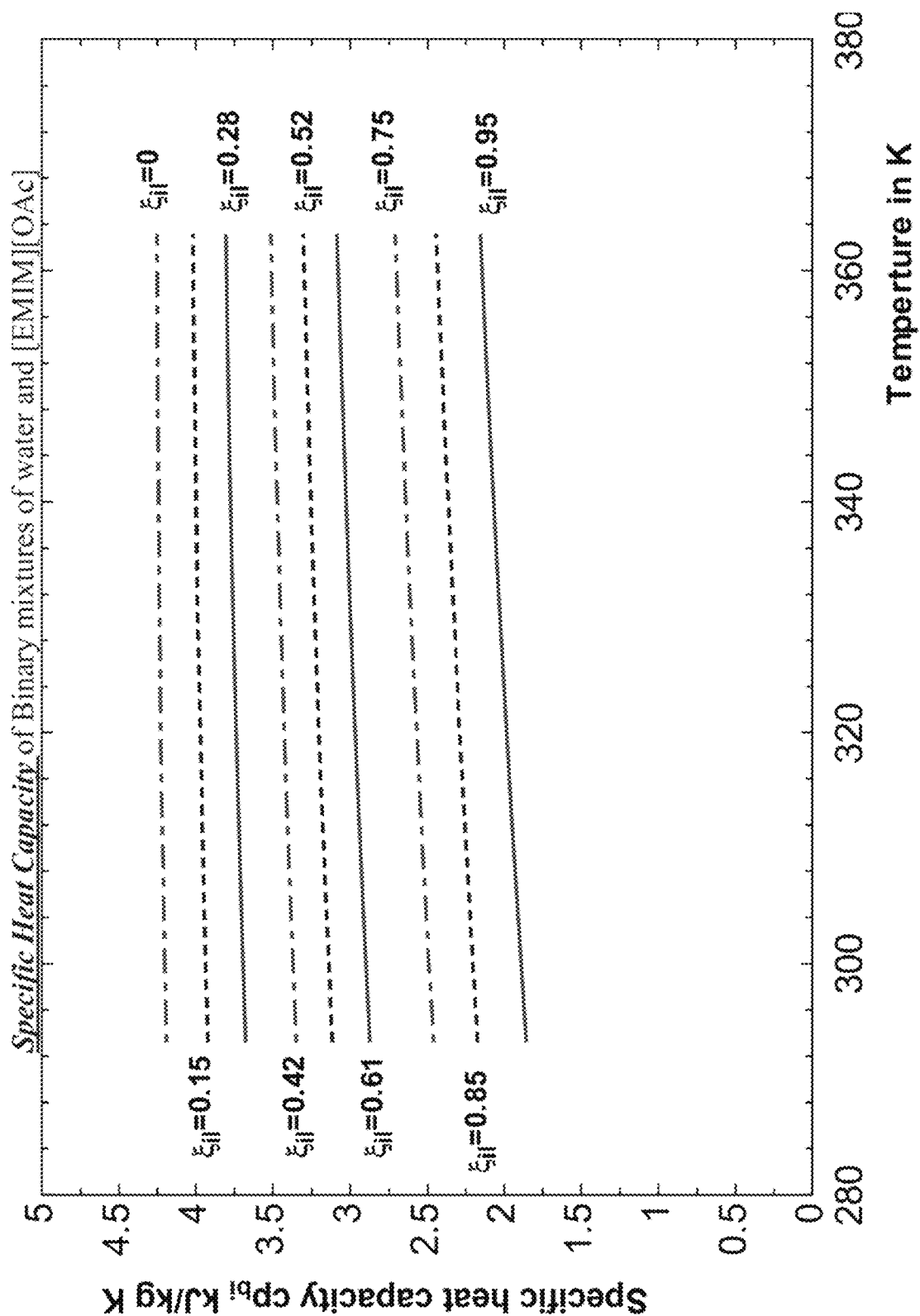
FIG. 5, from Qu, shows a graph of specific heat capacity versus temperature for mixtures of 1-Ethyl-3-methylimidazolium Acetate and Water.

FIG. 5, from Qu, shows a graph of specific heat capacity versus temperature for mixtures of 1-Ethyl-3-methylimidazolium Acetate and Water. The mole fraction of the 1-Ethyl-3-methylimidazolium Acetate is provided on the graph, wherein 0 is 100% water. The equation for the specific heat as a function of the mixture is provided below in Equation 1:

$$C_{p\_[EMIM][OAc]_{H_2O}} 2.761077 + 0.008120T - 1.106151 * 10^{-5} T^2 - 2.649514\xi - 0.918307\xi^2 + 0.003580T\xi \quad \text{Equation 1:}$$

Where, T is the binary temperature in K, and and $\xi$ is the mass fraction of EMIM.OAc.

Figure 6:
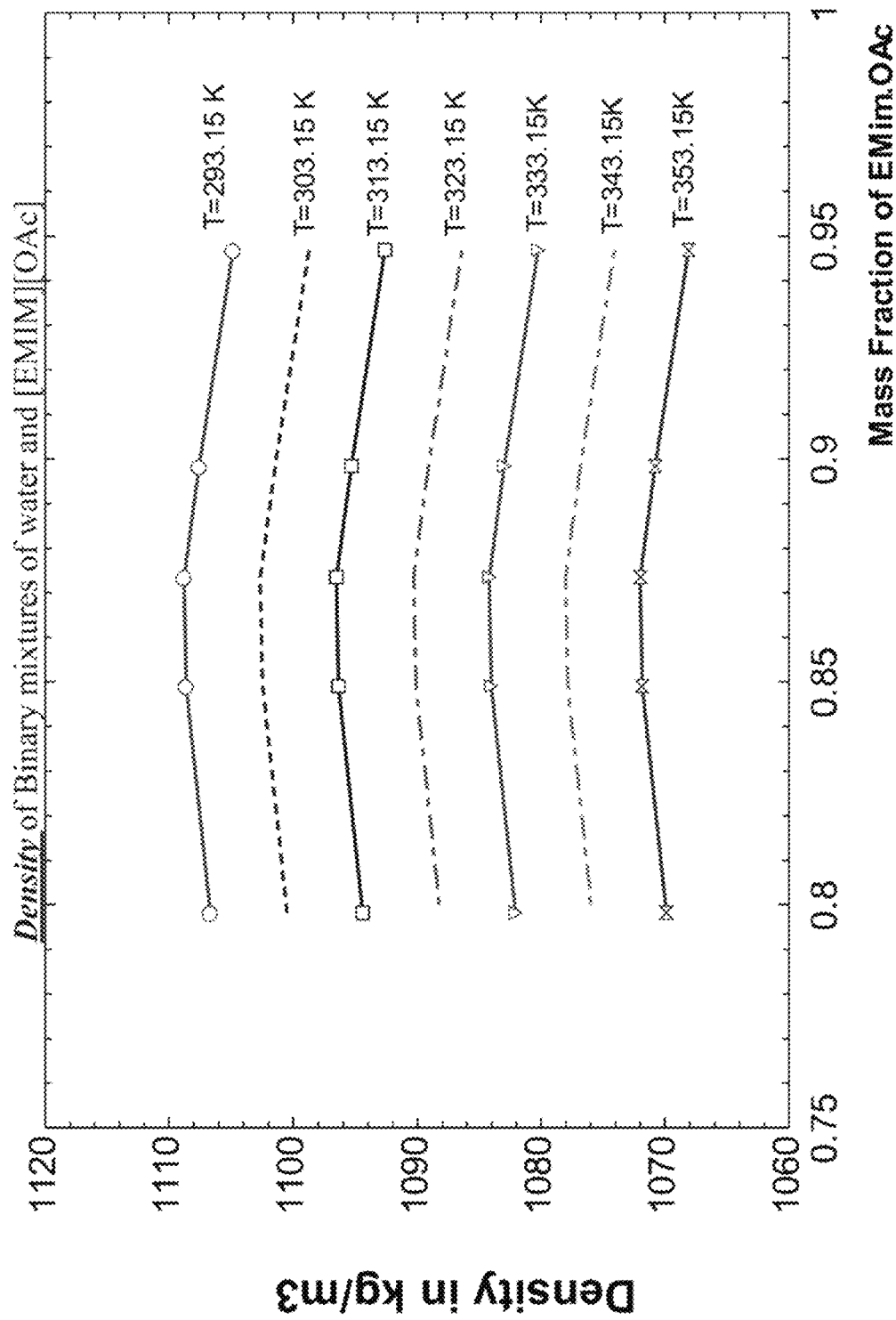
FIG. 6, from Qu, shows the density of binary mixtures of EMIM.OAc, as a function of the mass fraction of EMIM.OAc.

FIG. 6, from Qu, shows the density of binary mixtures of EMIM.OAc, as a function of the mass fraction of EMIM.OAc. The equation for density as a function of temparture, T in Kelvin and mass fraction of EMIM.OAc is provide in equation 2.

$$\rho_{[EMIM][OAc]_{H_2O}} = 1.012482*10^3 - 0.918103T + 6.25* 10^{-5} T^2 + 758.0905\xi - 497.846\xi^2 + 0.302582T\xi \quad \text{Equation 2}$$

Figure 7:
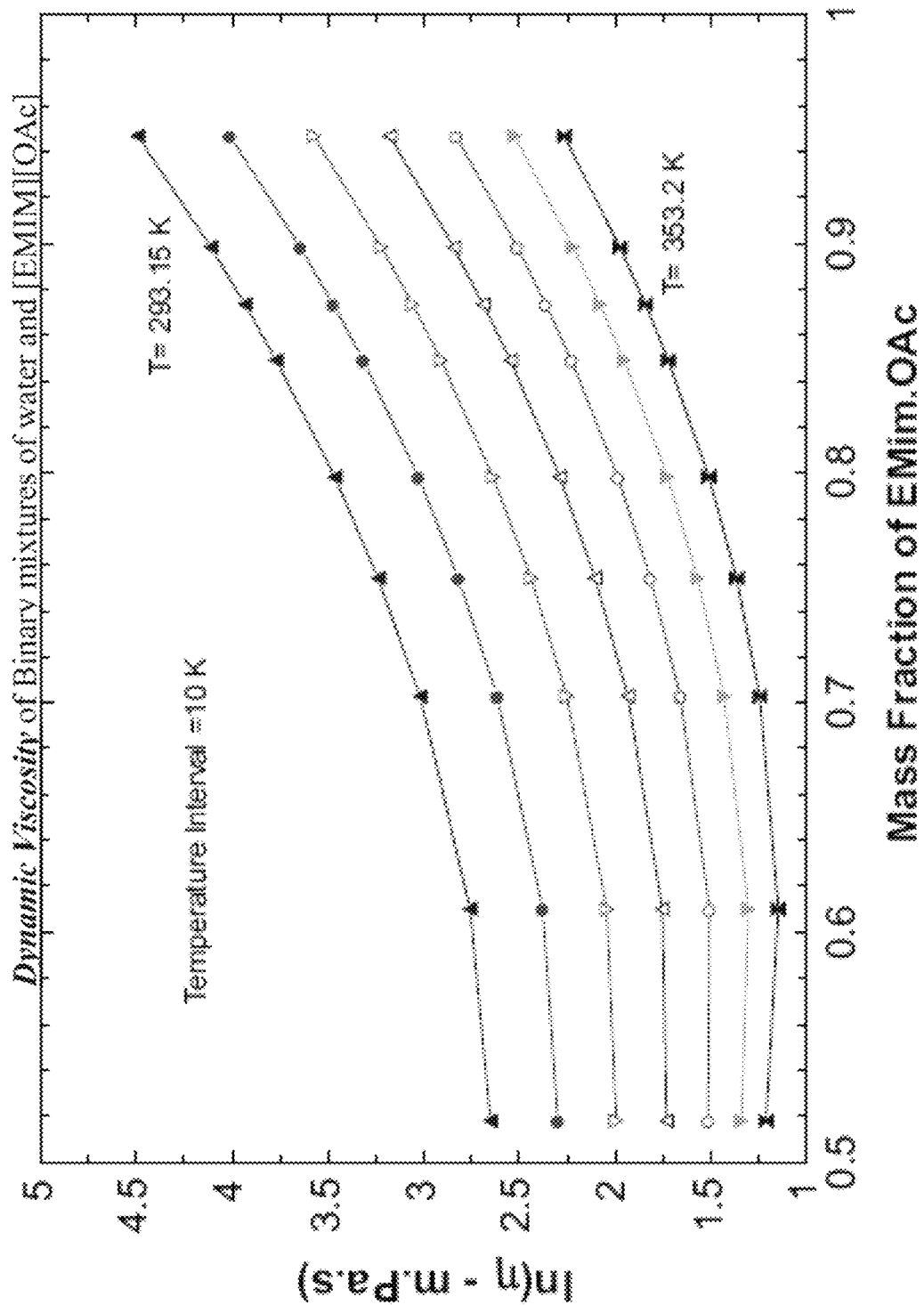
FIG. 7 shows the dynamic viscosities of aqueous solution of EMIM.OAc versus various temperatures and mass fractions of EMIM.OAc.

FIG. 7 shows the dynamic viscosities of aqueous solution of EMIM.OAc versus various temperatures and mass fractions of EMIM.OAc. The equation for dynamic viscosity is provided in Equation 3 where T is temperature in Kelvin and $\xi$ is the mass fraction of EMIM.OAc.

$$\text{Ln}(\eta_{[EMIM][OAc]\_H_2O}) = 3.025114 - 0.150834T + 2.20875*10^{-4} T^2 - 0.40864\xi - 9.363176\xi^2 + 0030720T\xi( \quad \text{Equation 3}$$

Figure 8:
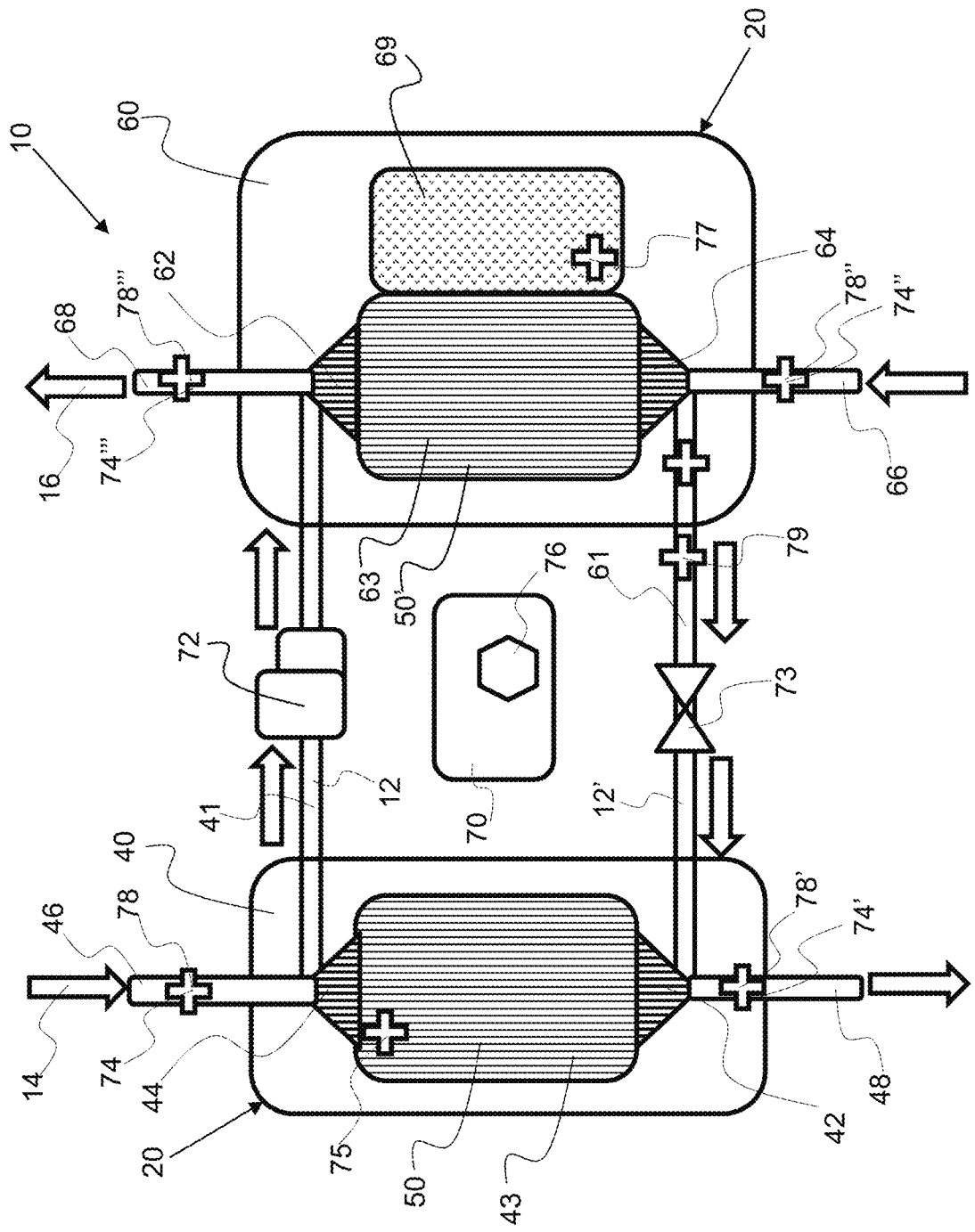
FIG. 8 shows an exemplary ionic liquid dehumidification system.

FIG. 8 shows an exemplary ionic liquid dehumidification system 10 comprising a conditioner 40 that removes moisture from a fluid, such as air, and a regenerator 60 that comprises a heating device 69 to remove the moisture in the ionic liquid desiccant 12. The ionic liquid desiccant flows in a loop from the conditioner to the regenerator through a post conditioner conduit 41 and from the regenerator to the conditioner through a post regenerator conduit 61. The conditioner comprises an exchanger 43 wherein the ionic liquid desiccant flows past an impermeable exchange membrane 50 on a first side, and the conditioner fluid 14, such as air, flows past the impermeable exchange membrane on a second and opposing side. Likewise, the conditioner comprises an exchanger 63 wherein the ionic liquid desiccant flows past an impermeable exchange membrane 50' on a first side, and the conditioner fluid 16, such as air, flows past the impermeable exchange membrane on a second and opposing side. An exemplary impermeable exchange membrane is an ionomer membrane comprising a proton conducting ionomer. The conditioner fluid 14 enters the conditioner through a fluid inlet 46 at an inlet humidity level and temperature and exits the conditioner through a fluid outlet 48 at an outlet humidity level and temperature. The conditioner fluid outlet humidity level of will be less than the conditioner fluid inlet humidity level as moisture from the conditioner fluid is absorbed into the ionic liquid desiccant through the impermeable exchange membrane 50 in the exchanger 43. The regenerator fluid 16 enters the regenerator through a fluid inlet 66 at an inlet humidity level and temperature and exits the regenerator through a fluid outlet 68 at an outlet humidity level and temperature. The regenerator fluid outlet humidity level will be higher than the regenerator fluid inlet humidity level as it absorbs moisture from the ionic liquid desiccant through the impermeable exchange membrane in the exchanger 63. An exchanger may comprise a plate and frame type exchanger that provides one or more channels for the flow of the ionic liquid desiccant and the conditioner fluid or regenerator fluid. A conditioner exchanger 43 may be a counter flow exchanger, as shown, wherein the ionic liquid desiccant inlet 42 and outlet 44 are opposite the inlet and outlet of the conditioner fluid 14. A regenerator exchanger 63 may be a counter flow exchanger, as shown, wherein the ionic liquid desiccant inlet 62 and outlet 64 are opposite the inlet and outlet of the conditioner fluid 16. An exchanger may be a tube-in-tube exchanger, wherein one of the conditioner or regenerator fluid flows around the tube and the ionic liquid desiccant flow within the tube. The tube may comprise, consist essentially of or consist of an impermeable exchange membrane. An exemplary conditioner may be part of a cooling system 20 for an air cooling system for a dwelling, for example. The exemplary ionic liquid dehumidification system comprises a controller 70 for controlling the functions of the system, such as controlling a pump 72 and/or a valve 73 for the ionic liquid desiccant flow. A controller may interface with sensors, such a humidity sensors 78-78''' and/or temperature sensors 74-74''' to determine a flow rate of the ionic liquid desiccant. A flow sensor 79 may provide input to the controller of the flow rate of the ionic liquid desiccant. A temperature sensor 77 may be used to determine the temperature of the ionic liquid desiccant and/or a temperature produced by the heating device 69. A controller may have a microprocessor 76 that runs a computer program to control the functions of the system.

Figure 9:
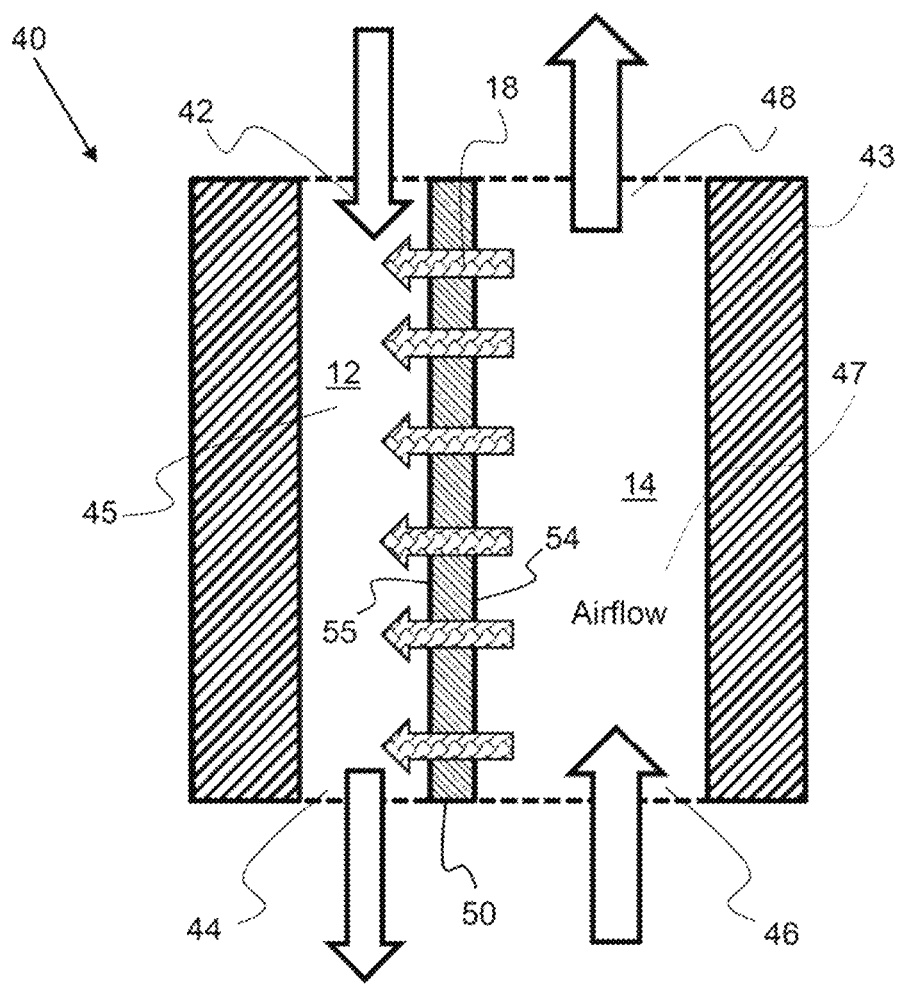
FIG. 9 shows a diagram of an exemplary conditioner.

As shown in FIG. 9, an exemplary conditioner 40 comprises a conditioner fluid conduit 47 for the flow of a conditioner fluid 14 on a conditioner side 54 of an impermeable exchange membrane 50 and an ionic liquid desiccant conduit 45 for the flow of ionic liquid desiccant 12 on the ionic liquid desiccant side 55 of the impermeable exchange membrane 50. Water 18 is transferred through the impermeable exchange membrane 50 from the conditioner fluid 14 to the ionic liquid desiccant 12. The exchanger is a counter flow exchanger wherein the inlet 46 and out 48 of the conditioner fluid 14 are opposite the inlet 42 and outlet 44 of the ionic liquid desiccant 12.

Figure 10:
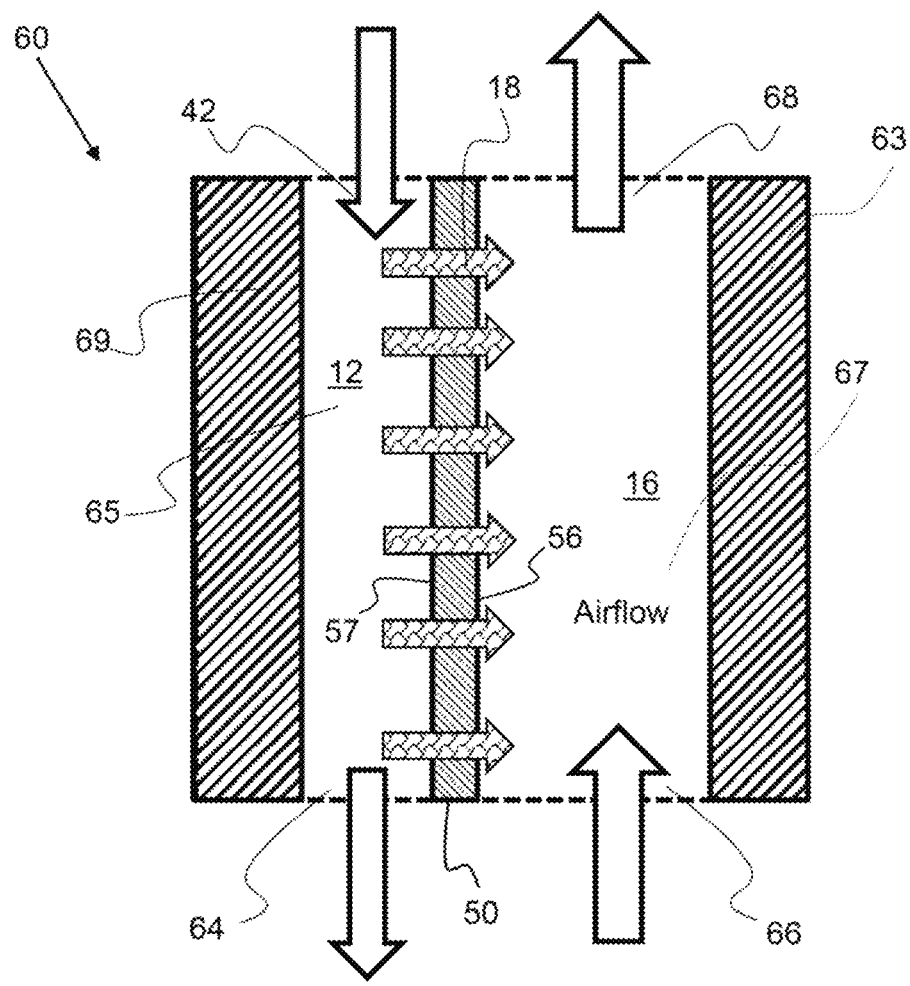
FIG. 10 shows a diagram of an exemplary regenerator.

As shown in FIG. 10, an exemplary regenerator 60 comprises a regenerator fluid conduit 67 for the flow of a regenerator fluid 16 on a regenerator side 64 of an impermeable exchange membrane 50 and an ionic liquid desiccant conduit 65 for the flow of ionic liquid desiccant 12 on the ionic liquid desiccant side 57 of the impermeable exchange membrane 50. Water 18 is transferred through the impermeable exchange membrane 50 from the ionic liquid desiccant 12 to the regenerator fluid 16. The exchanger is a counter flow exchanger wherein the inlet 66 and out 68 of the regenerator fluid 16 are opposite the inlet 62 and outlet 64 of the ionic liquid desiccant 12.

Figure 12:
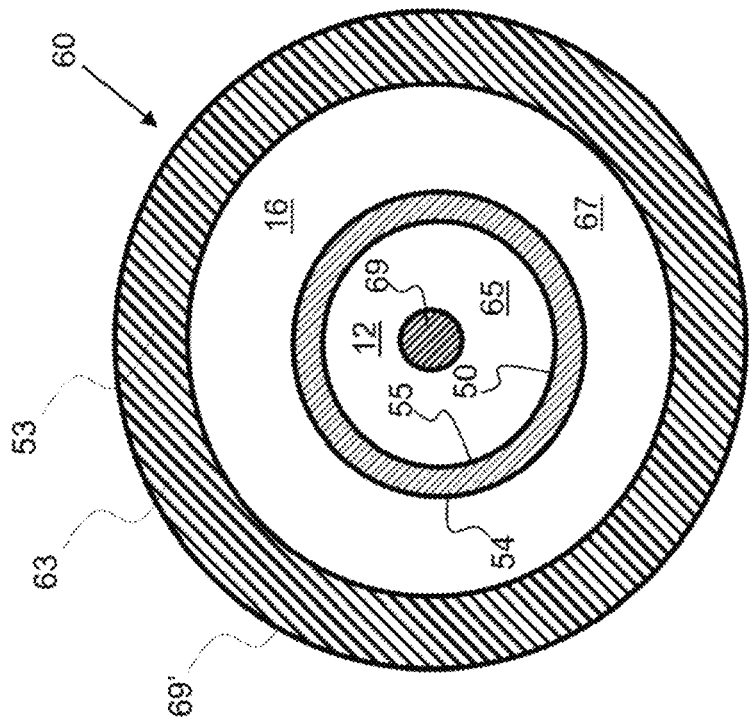
FIGS. 11 and 12 show exemplary tube-in-tube exchangers.
Figure 11:
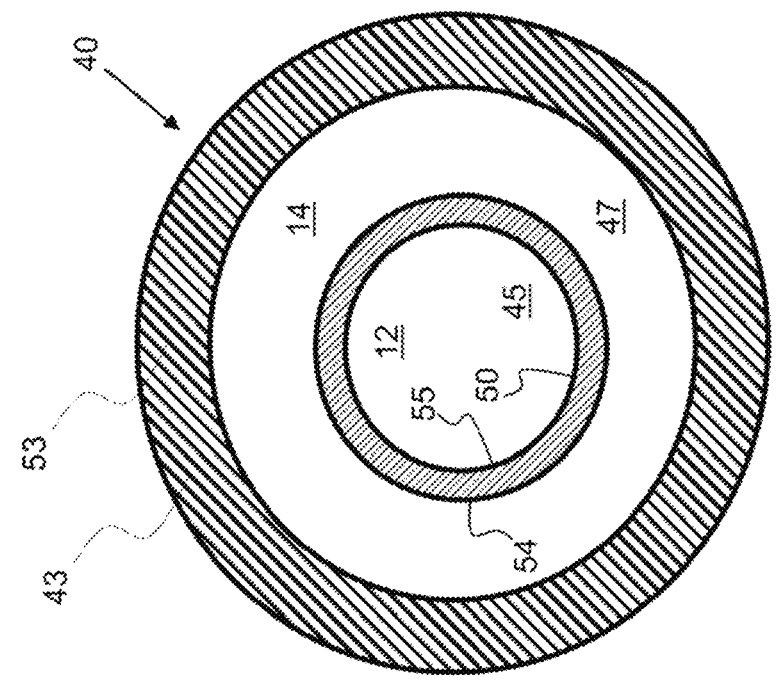

As shown in FIGS. 11 and 12, an exchanger may be a tube-in-tube exchanger. FIG. 11 shows an exemplary conditioner 40 comprising a conditioner exchanger 43 that is a tube-in-tube exchanger 53 having a conditioner fluid conduit 47 configure around an ionic liquid desiccant conduit 45. FIG. 12 show a regenerator exchanger 63 that is a tube-in-tube exchanger 53 having a regenerator fluid conduit 67 around an ionic liquid desiccant conduit 65. The exemplary regenerator 60 has a heating device 69 within the ionic liquid desiccant conduit 65 and optionally may have a heating device 69' around the regenerator fluid conduit. The entire tube-in-tube exchanger may flow through a heating device.

Figure 13:
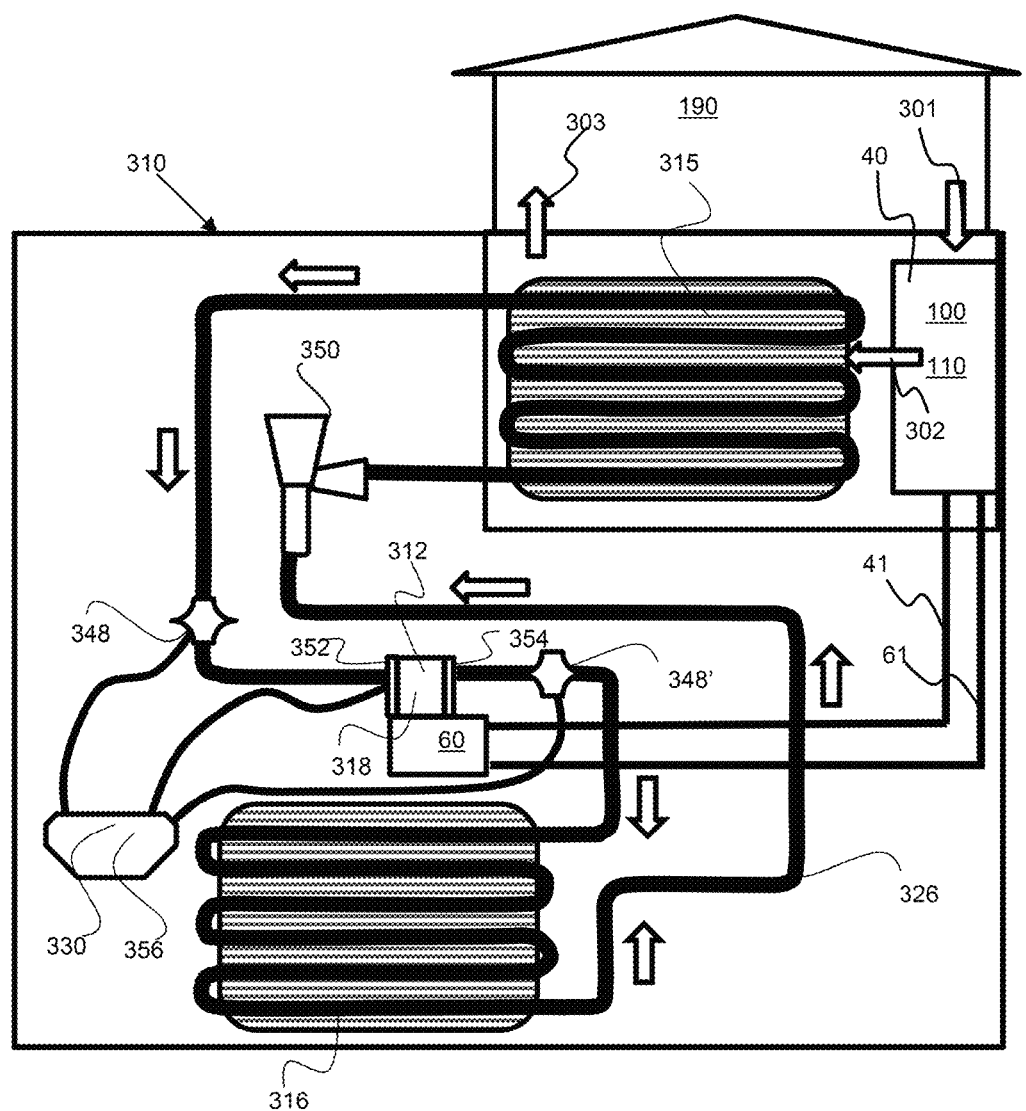
FIG. 13 shows a diagram of an exemplary refrigerant system comprising an exemplary ionic liquid desiccant dehumidification system.

As shown in FIG. 13. an exemplary refrigeration system 310 comprises a compressor 318 a condenser 316 and expansion valve 350 and an evaporator 315. The evaporator cools the air before it enters into an enclosure 190. A liquid ionic desiccant system 100 is configured to reduce the moisture content of the incoming air 301 into the desiccant chamber. The outlet air 302 from the desiccant chamber will have a lower moisture content than the incoming air. The air entering the enclosure 303 will be cool and dry. The enclosure shown is a home. Note that the desiccant chamber may be configured before or after the evaporator or cooling device. The compressor has a low pressure side 352 and a high pressure side 354. The compressor may be a mechanical compressor or an electrochemical compressor 312 comprising a membrane electrode assembly 314. The refrigeration system has a plurality of sensors 348, a controller 330 that may run a control program 356 on a microprocessor, for example. The conditioner 40 comprises a liquid ionic desiccant 110 that absorbs moisture from the incoming air 301. The airflow through the conditioner 40 portion of the ionic liquid dehumidification system reduces the moisture content of the air flow 303 entering the dwelling 190 and the evaporator 315 further cools the air. The ionic liquid dehumidification system 10 has a regenerator 60 that may be configured to absorb heat from the compressor 318 to drive moisture from the ionic liquid desiccant. The regenerator may be in thermal contact with the compressor 318 and may be physically coupled to the compressor such as by a heat exchanger. Conduits 41 and 61 transfer the ionic liquid desiccant between the conditioner and the regenerator. Conduits 326 transport the working fluid through the refrigeration system.

Figure 14:
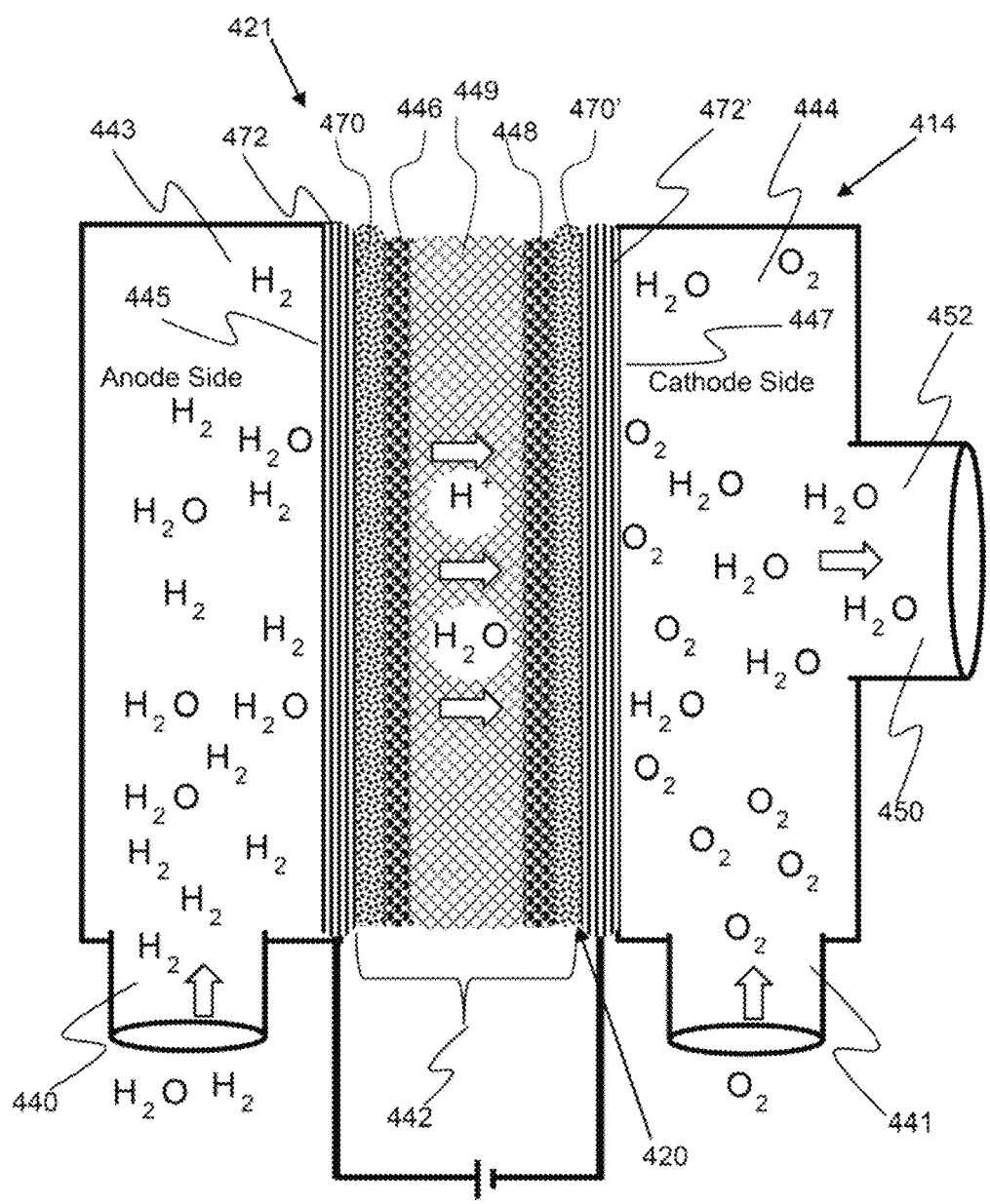
FIG. 14 shows an exemplary fuel cell.

FIG. 14 shows an exemplary fuel cell having an ion conducting layer separating an anode from a cathode. The ion conducting layer may comprise an ionomer and may be a composite ionomer membrane comprising a support material, such as a fluoropolymer membrane. An exemplary fuel cell may be used in a refrigeration system and may be a heating device for the regenerator in an ionic liquid dehumidification system. Power produced by the fuel cell may be used to power portions of the ionic liquid dhimmification system. As shown in FIG. 14, an electrochemical compressor 421 comprises a fuel cell 414 having an anode 446, an ion conductive membrane 449 and a cathode 48. Water is introduced on the anode side 445 and is converted into protons, $H^+$, that are transported across the ion conducting membrane 449 to the cathode side 447. A gas diffusion media 470, 470' is configured in direct and electrical contact with the anode and cathode respectively. An exemplary fuel cell 414 comprises an electrochemical cell 420. The fuel cell comprises a membrane electrode assembly 442 comprising a proton conducting membrane 449, an anode 446 and cathode 448. A membrane electrode assembly may in some cases include a gas diffusion media 470, 470'. A flow field 472, 472', typically comprising an electrically conductive plate having channels for the delivery of gasses to the surface of the membrane electrode assembly, is configured on either side of the membrane electrode assembly. The anode side 445 of the fuel cell converts hydrogen to protons, $H^+$, which are then transported across the membrane to the cathode side 447. At the cathode, the protons react with oxygen to produce water and the water produced moves through the compressor outlet 452 and into conduit 450. This transfer, or pumping, of protons across the membrane produces an increased pressure on the cathode side. The anode side 445 is the low pressure side 443, and the cathode side 447 is the high pressure side 444 of the electrochemical compressor 420. The hydrogen inlet 440 and oxygen inlet 441 are shown. A fuel cell produces heat and this heat may be used in a regenerator and may be a heating device in a ionic liquid dehumidification system as described herein.

Figure 15:
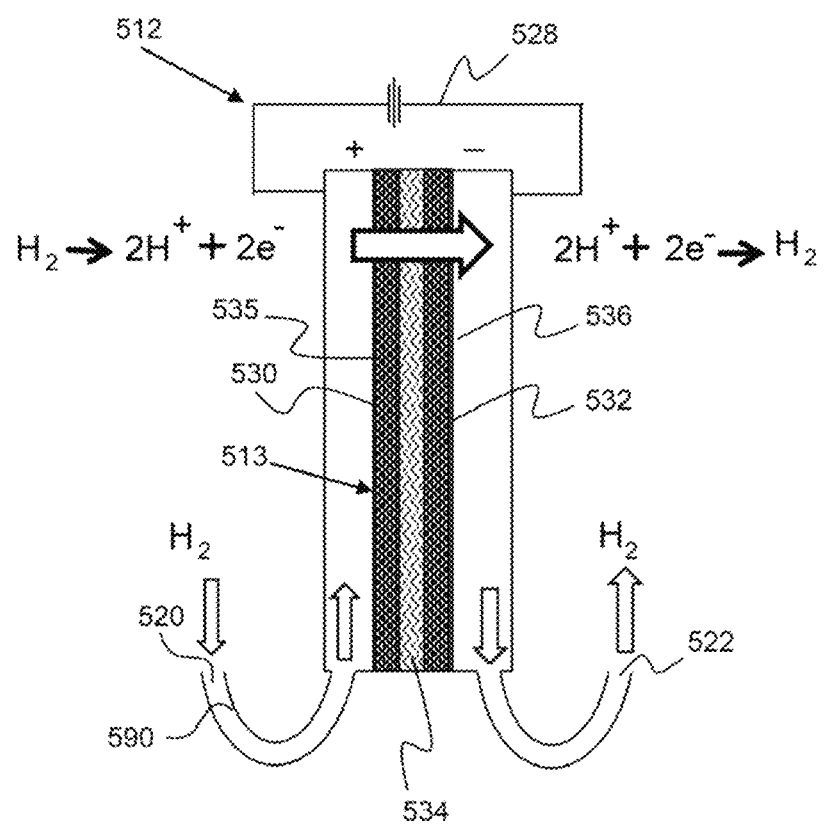
FIG. 15 shows an exemplary hydrogen pump.
Figure 16:
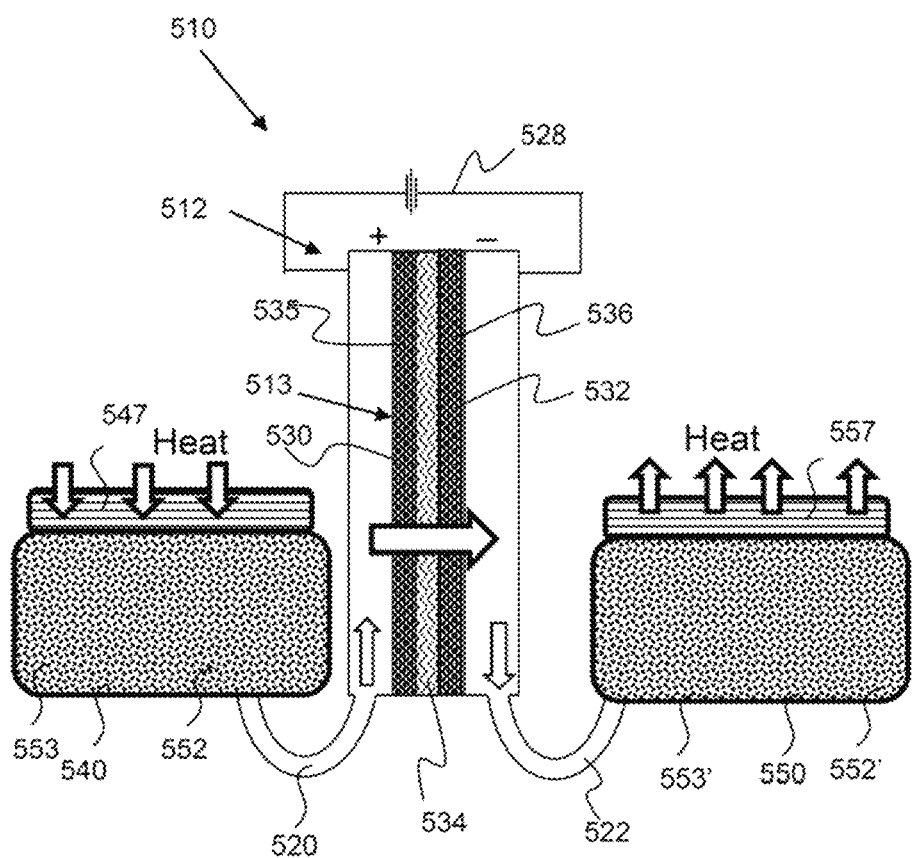
FIG. 16 shows an exemplary metal hydride heating system.

Referring now to FIGS. 15 and 16, FIG. 15 shows a diagram of an electrochemical hydrogen pump 512, or electrochemical compressor, that may be used as an electrochemical compressor. A proton associable fluid 590 may be pumped through the ion conducting layer 534 from an anode side 535 to a cathode side 536, or from an inlet 520 to an outlet 522, on a high pressure side. The anode 530 and cathode 532 are coupled by a power source 528 that drives the reactions. The membrane electrode assembly 513 may comprise an ionomer or ionomer membrane. The electrochemical compressor may be used in a refrigeration system and may be a heating device for the regenerator in an ionic liquid dehumidification system.

As shown in FIG. 16, an exemplary metal hydride electrochemical heat transfer device 510 that comprises an electrochemical hydrogen compressor 512. The electrochemical compressor 512 pumps hydrogen from an anode side 535, and from a first metal hydride reservoir 540 across the membrane electrode assembly 513 to the cathode side 536 and into a second metal hydride reservoir 550 such as a tank or enclosure for the metal hydride forming alloy 553 material. The metal hydride 552 material may be a packed bed or a monolith for example. The metal hydride reservoir may comprise an additive such as fluoropolymer, silica or metal such as copper, to aid in expansion and contraction of the metal hydride. The compressor may be reversed, wherein the controller changes the potential of the power supply 528 to switch the anode to the cathode the cathode to the anode. In this way, hydrogen can be pumped back and forth between the two metal hydride reservoirs. Heat transfer devices 547, 557 are coupled to the metal hydride portion 540, 550 respectively. The heat transfer device may transfer heat to and/or from the metal hydride reservoir to an article or to the air or environment. A heat transfer device may comprise fins, a conduit for a flow of a heat transfer fluid, a conducting plate, and the like. A heat transfer device may be thermally coupled with a regenerator of an ionic liquid desiccant dehumidification system, as described herein.

Figure 17:
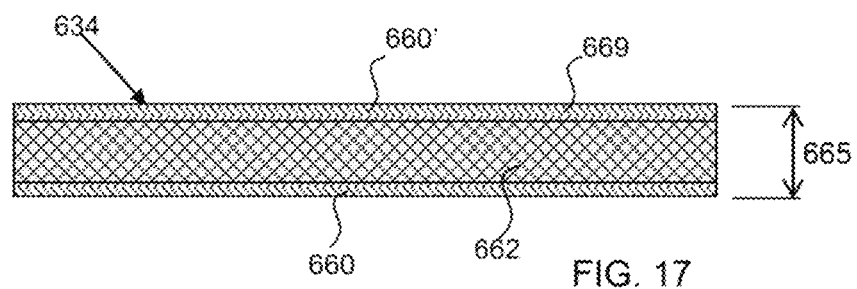
FIG. 17 to 19 show cross-sections of exemplary impermeable exchange membrane.
Figure 18:
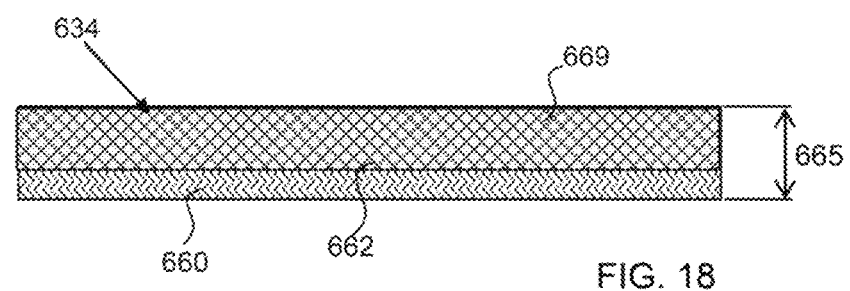
Figure 19:
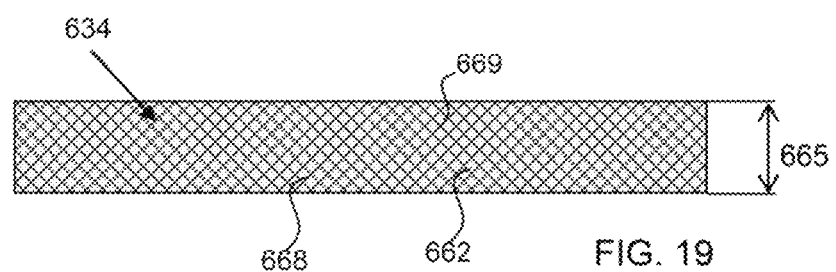

As shown in FIGS. 17 through 19, an ionomer layer 634 is a composite ionomer membrane 669 having a reinforcing material 662. The reinforcing material 662, such as a membrane or discrete reinforcing elements or fibers, may be configured within the ionomer 660, wherein the ionomer is exposed on either side of the reinforcing material, as shown in FIG. 17. In an alternative embodiment, the reinforcing material is configured to one side of the composite ionomer membrane 669, as shown in FIG. 18. In another embodiment, the reinforcing material 662 extends through the thickness 665 of the composite ionomer membrane 669, wherein there is substantially no ionomer layer on the top or bottom surface, as shown in FIG. 19. The composite ionomer membrane may be very thin to enable quick transfer of hydrogen and therefor a higher heating flux rate. The composite ionomer membrane may be about 30 µm or less, about 25 µm or less, about 20 µm or less, about 15 µm or less, about 10 µm or less, about 5 µm or less. The ionomer 60 interpenetrates the reinforcing material 62. The ionomer and/or the composite ionomer may have an additive 668, to improve performance such as silica or other desiccant particles, or reinforcing materials, as described herein.

Figure 20:
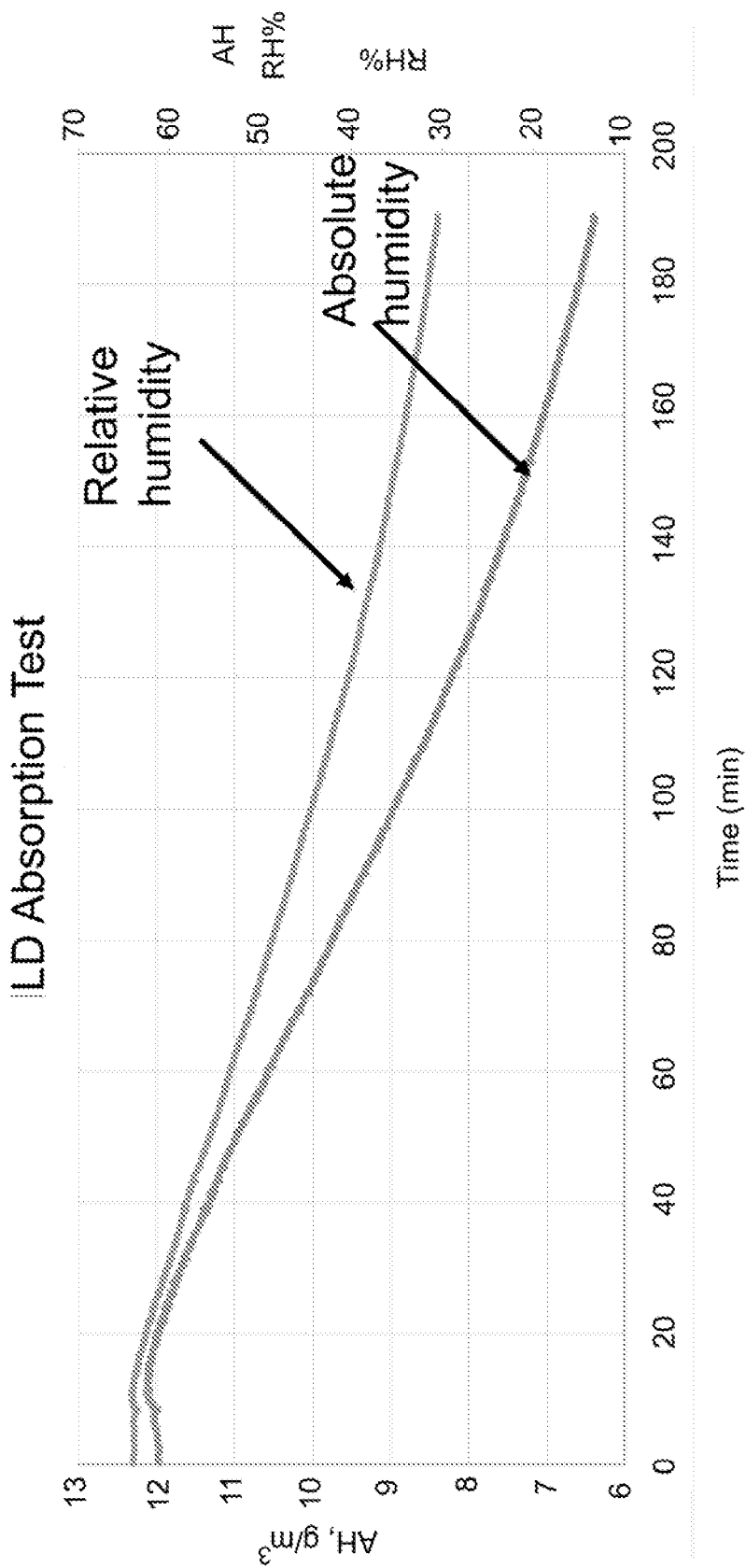
FIGS. 20 and 21 show test results of humidity versus time for an exemplary test ionic liquid dehumidification system.
Figure 21:
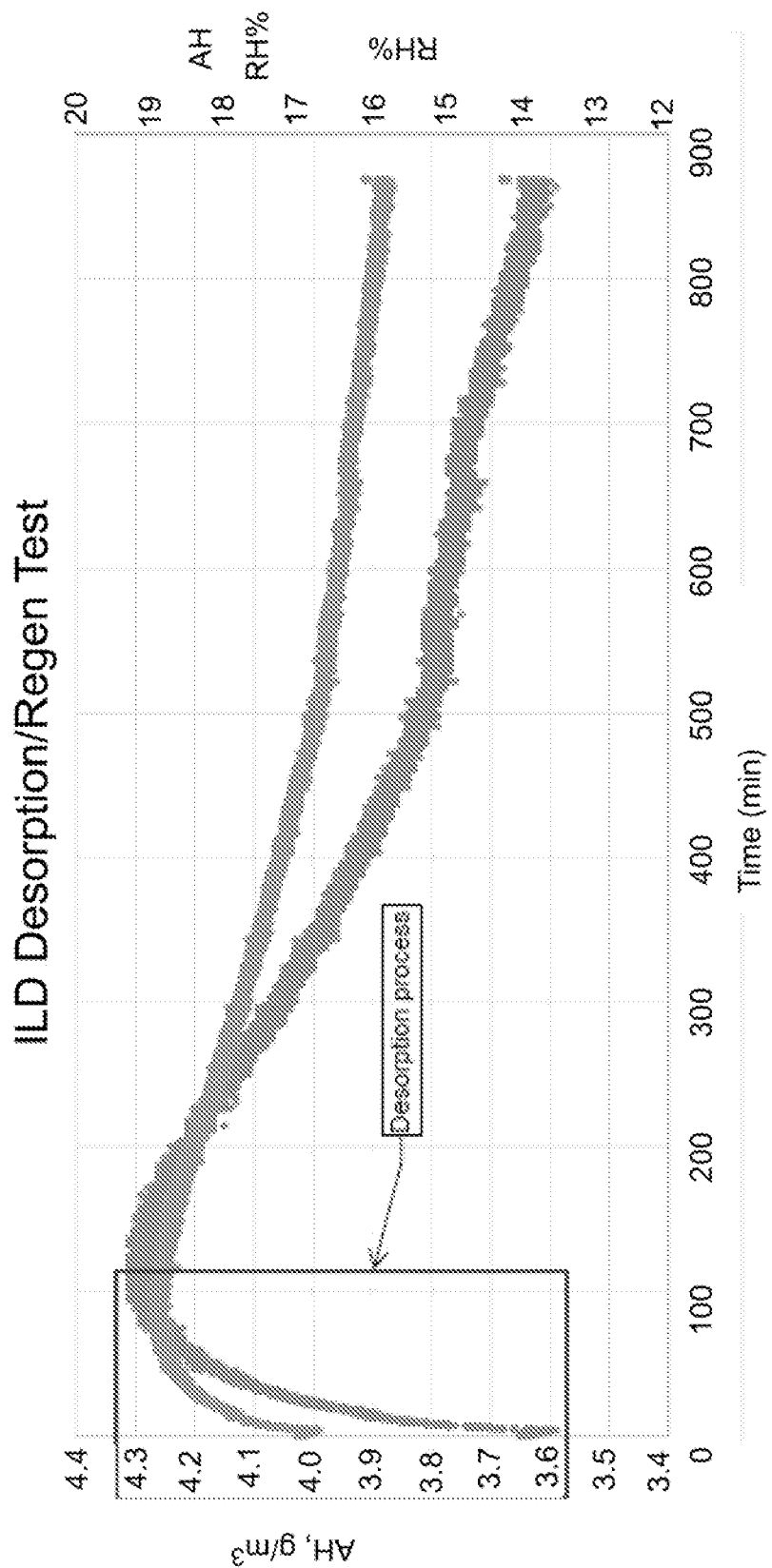

As shown in FIGS. 20 and 21, a test apparatus was constructed to measure the rate of moisture transfer through an impermeable exchange membrane, Nafion 211, or a perfluorosulfonic acid polymer that was approximately 25 microns thick, and 1100 equivalent weight. The test chamber was 40.6 cm cubed and one side had a 588 cm2 impermeable exchange membrane configured between the chamber and a flow of ionic liquid desiccant. The ionic liquid desiccant was IoLiTech Ionic Liquids Technologies, GmbH, as was the 1-Ethyl-3-methylimidazolium acetate [EMIM][OAc]. The test ILD weight was 194.6 g, density 1.1 g/cc, and 95% concentration. For the absorption portion of the test, wherein moisture was absorbed from the chamber into the ionic liquid desiccant through the membrane, the inlet mass flow rate of the ionic liquid desiccant was 0.620 g/c and the outlet mass flow rate was 0.337 g/s. The airflow rate through the chamber was 1.12×10-04 CFM. For the desorption test, the aiflow rate was 1.12×10-04 CFM, the ILD inlet mass flowrate was 0.837 g/s and the outlet mass flowrate was 0.415 g/s. FIG. 20 shows the rate of relative and absolute humidity drop as the ionic liquid desiccant flowed past the exchange membrane to absorb moisture from the test chamber. FIG. 21 show a desorption of the moisture from the ionic liquid desiccant back into the chamber, wherein the ionic liquid desiccant was heated in this phase to promote the desorption of the moisture from the ionic liquid desiccant. The benchtop prototype for desiccating an ionic liquid desiccant (ILD) had a plurality of channels for exchanging moisture from the ILD with dry gas, such as air. The benchtop prototype produced a confirmed savings of about 21% of the energy required for HVAC applications based on our small-scale prototype. At the heart of this demonstration unit was a 'ionic membrane' contactor in a plate and frame type arrangement that provided an active surface for moisture absorption and desorption. In testing, we determined that the ionic salts are corrosive in nature, requiring careful selection of materials of construction. For highest performance, the desiccant system required large surface area relative to the ionic salt mass.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:
1. A cooling system comprising an ionic liquid dehumidification system comprising:
 a) an ionic liquid desiccant composition comprising:
   i) an ionic liquid desiccant;
   ii) water;
 b) a conditioner comprising:
   i) a conditioner ionic liquid desiccant conduit having:
     an ionic liquid desiccant inlet;
     an ionic liquid desiccant outlet;
     wherein the ionic liquid desiccant composition flows through the conditioner ionic liquid desiccant conduit;
   ii) a conditioner fluid conduit having:
     a conditioner fluid inlet;
     a conditioner fluid outlet;
     wherein a conditioner fluid flows through the conditioner fluid conduit; and
   iii) an impermeable exchange membrane configured between the conditioner ionic liquid desiccant conduit and the conditioner fluid conduit;
   wherein the conditioner fluid comprises moisture that is transferred through the conditioner impermeable exchange membrane to the ionic liquid desiccant flowing through the conditioner ionic liquid desiccant conduit;
 c) a regenerator;
   i) a regenerator ionic liquid desiccant conduit having:
     an ionic liquid desiccant inlet;
     an ionic liquid desiccant outlet;
     wherein the ionic liquid desiccant composition flows through the regenerator ionic liquid desiccant conduit;
   ii) a regenerator fluid conduit having:
     a regenerator fluid inlet;
     a regenerator fluid outlet;

wherein the regenerator fluid flows through the regenerator fluid conduit;

i) an impermeable exchange membrane configured between the regenerator ionic liquid desiccant conduit and the regenerator fluid conduit;

d) a heater that heats the ionic liquid desiccant so that ionic liquid desiccant is heated to a temperature greater than the temperature of ionic liquid desiccant in the conditioner.

2. The cooling system of claim 1, wherein the ionic liquid desiccant is an organic ionic salt.

3. The cooling system of claim 2, wherein the organic ionic salt is 1-Ethyl-3-methylimidazolium acetate [EMIM][OAc].

4. The cooling system of claim 2, wherein the organic ionic salt composition is configured in a binary mixture with water.

5. The cooling system of claim 1, wherein the heater comprises a compressor and wherein the cooling system is coupled with a refrigeration system that comprises said compressor and further comprises:

a) a condenser;
b) an evaporator; and
c) an expansion valve, and wherein the compressor of the refrigeration system heats the ionic liquid desiccant.

6. The cooling system of claim 1, further comprising a fuel cell to provide electrical power to the cooling system.

7. The cooling system of claim 6, wherein the fuel cell heats the ionic liquid desiccant in the regenerator.

8. The cooling system of claim 7, wherein the fuel cell is a polymer electrolyte fuel cell comprising an ionomer membrane.

9. The cooling system of claim 1, wherein the heater comprises an electrochemical compressor comprising a polymer electrolyte membrane and wherein the polymer electrolyte membrane comprises an ionomer.

10. The cooling system of claim 1, wherein the impermeable exchange membrane comprises an ionomer.

11. The cooling system of claim 10, wherein the impermeable exchange membrane has a Gurley value of more than 500 seconds.

12. The cooling system of claim 1, wherein the conditioner is configured as a tube-in-tube exchanger with the impermeable exchange membrane configured between the conditioner fluid conduit and the conditioner ionic liquid desiccant conduit in the tube-in-tube exchanger.

13. The cooling system of claim 12, wherein the conditioner fluid conduit is configured around the in conditioner ionic liquid desiccant conduit.

14. The cooling system of claim 1, wherein the regenerator is configured as a tube-in-tube exchanger with the impermeable exchange membrane configured between the conditioner fluid conduit and the conditioner ionic liquid desiccant conduit in the tube-in-tube exchanger.

15. The cooling system of claim 14, wherein the regenerator fluid conduit is configured around the in regenerator ionic liquid desiccant conduit.

16. The cooling system of claim 14, further comprising a heating device configured within the regenerator ionic liquid desiccant conduit to heat the ionic liquid desiccant composition within the tube-in-tube exchanger.

17. A cooling system comprising an ionic liquid dehumidification system comprising:

a) an ionic liquid desiccant composition comprising:
  i) an ionic liquid desiccant;
b) a conditioner comprising:
  wherein the ionic liquid desiccant composition flows through the conditioner;
  i) a conditioner fluid conduit;
  wherein a conditioner fluid flows through the conditioner fluid conduit; and
  ii) an impermeable exchange membrane configured between the conditioner and the conditioner fluid conduit;
c) a regenerator;
  i) a regenerator ionic liquid desiccant;
  wherein the ionic liquid desiccant composition flows through the regenerator ionic liquid desiccant conduit;
  ii) a regenerator fluid conduit;
  wherein a regenerator fluid flows through the regenerator fluid conduit;
  ii) an impermeable exchange membrane configured between the regenerator and the regenerator fluid conduit;
d) a metal hydride electrochemical heat transfer device that heats the ionic liquid desiccant.

18. The cooling system of claim 17, wherein the metal hydride electrochemical heat transfer device comprises an electrochemical pump for pumping hydrogen to an enclosure comprising metal hydride.

19. The cooling system of claim 17, wherein the conditioner further comprises a conditioner ionic liquid desiccant conduit and wherein the conditioner is configured as a tube-in-tube exchanger with the impermeable exchange membrane configured between the conditioner fluid conduit and the conditioner ionic liquid desiccant conduit in the tube-in-tube exchanger.

20. The cooling system of claim 17, wherein the regenerator further comprises a regenerator ionic liquid desiccant conduit and wherein the regenerator is configured as a tube-in-tube exchanger with the impermeable exchange membrane configured between the conditioner fluid conduit and the conditioner ionic liquid desiccant conduit in the tube-in-tube exchanger.

* * * * *